United States Patent [19]
Houdi et al.

[11] Patent Number: 6,150,420
[45] Date of Patent: Nov. 21, 2000

[54] METHOD FOR ENHANCED BRAIN DELIVERY OF BUPROPION

[75] Inventors: Abdulghani A. Houdi; Anwar A. Hussain, both of Lexington, Ky.

[73] Assignee: Theramax, Inc., Lexington, Ky.

[21] Appl. No.: 09/235,833

[22] Filed: Jan. 22, 1999

Related U.S. Application Data

[63] Continuation of application No. 09/087,994, Jun. 1, 1998.
[51] Int. Cl.⁷ .................................................. A61K 31/135
[52] U.S. Cl. .............................................. 514/649
[58] Field of Search ............................................. 514/649

[56] References Cited

U.S. PATENT DOCUMENTS

| | | |
|---|---|---|
| 3,819,706 | 6/1974 | Mehta . |
| 3,885,046 | 5/1975 | Mehta . |
| 4,021,492 | 5/1977 | Linder et al. . |
| 4,177,291 | 12/1979 | Lindberg et al. . |
| 4,308,400 | 12/1981 | Felder et al. . |
| 4,347,257 | 8/1982 | Stern . |
| 4,393,078 | 7/1983 | Peck . |
| 4,425,363 | 1/1984 | Stern . |
| 4,435,449 | 3/1984 | Stern . |
| 4,507,323 | 3/1985 | Stern . |
| 4,816,489 | 3/1989 | Lafon . |
| 4,980,377 | 12/1990 | Lafon . |
| 5,236,922 | 8/1993 | Lafon . |
| 5,358,970 | 10/1994 | Ruff et al. . |
| 5,427,798 | 6/1995 | Ludwig et al. . |
| 5,541,231 | 7/1996 | Ruff et al. . |
| 5,561,149 | 10/1996 | Azria et al. . |
| 5,567,682 | 10/1996 | Pert . |
| 5,578,567 | 11/1996 | Cardinaux et al. . |
| 5,589,460 | 12/1996 | Abajian et al. . |
| 5,603,943 | 2/1997 | Yanagawa . |
| 5,624,898 | 4/1997 | Frey, II . |
| 5,629,011 | 5/1997 | Illum . |
| 5,792,799 | 8/1998 | Sherman-Gold . |

OTHER PUBLICATIONS

Hsyu et al J Chen Pharmacol, vol. 37, pp. 737–743, 1997.
Medical Letter vol. 37, issue 940 pp. 6–8, Jan. 20, 1995.
Robinson et al. Am J. Hosp Pharm 48(10 suppl) abstract, Oct. 1991.

*Primary Examiner*—Rebecca Cook
*Attorney, Agent, or Firm*—Burns, Doane, Swecker & Mathis, L.L.P.

[57] ABSTRACT

This invention provides to a method for enhancement of delivery of bupropion by administration via the nasal route, and methods of treatment comprising intranasal administration of bupropion. The present invention further provides pharmaceutical compositions comprising bupropion and/or pharmaceutically acceptable salts thereof.

23 Claims, 3 Drawing Sheets

(R)-Bupropion (S)-Bupropion

METHOD FOR ENHANCED BRAIN DELIVERY OF BUPROPION

This application claims priority under 35 U.S.C. §§119 and/or 365 to U.S. Ser. No. 09/087,994 filed on Jun. 1, 1998; the entire content of which is hereby incorporated by reference.

BACKGROUND OF THE INVENTION

1. Field of the Invention

This invention relates to a method for enhancement of delivery of bupropion by administration via the nasal route, and methods of treatment comprising intranasally administering an effective amount of bupropion to prevent or treat withdrawal symptoms associated with smoking nicotine to a patient in need of such prevention or treatment and for the treatment of depression.

2. Description of the Related Art

Bupropion (1-[3-Chlorophenyl]-2-[(1,1-dimethylethyl) amino]-1-propanone) is a relatively dopamine-specific antidepressant of the aminoketone class (FIG. 1). It is chemically unrelated to the classical tricyclic antidepressants, but its therapeutic efficacy is comparable to the tricyclic antidepressant. In addition to its antidepressant properties, bupropion has been found to curb the craving and withdrawal symptoms tobacco smokers face when they quit (Ferry, L. H. et al. (1994) *J. Addict. Dis.* 13:249; Hurt, R. D. et al. (1997) *N. Engl. J. Med.* 337:1195). Bupropion was approved for use as an antidepressant by the Food and Drug Administration in 1989. It is currently marketed under the trade names Wellbutrin® (Burroughs Wellcome) and Zyban® (Glaxo-Wellcome).

Bupropion is well absorbed from the gastrointestinal tract after oral administration and is extensively metabolized in rat and man prior to excretion (9,10). Evidence suggests that bupropion has fewer autonomic and cardiovascular side effects than the tricyclic antidepressants (3–6). The three principal metabolites, hydroxybupropion, threohydrobupropion, and erythrohydrobupropion appear to have slower clearance than bupropion, therefore they tend to accumulate to a greater extent than the parent drug during chronic bupropion therapy (10). It has been suggested that during chronic bupropion therapy, high hydroxybupropion concentrations may be associated with poorer clinical outcome (11,12). Furthermore, bupropion therapy is associated with seizures in approximately 0.4% of the patients treated with doses up to 450 mg/day. The incidence of seizures may exceed those of other antidepressants by up to fourfold, increasing to approximately tenfold at doses of 450–600 mg/day (7,8).

Combination therapy is often necessary in the treatment of mood disorders. Nevertheless, there are few data available regarding interactions between bupropion and other drugs. Clinical evidence suggests that the co-administration of fluoxetine (Prozac) and bupropion may yield delirium (13) and seizures (14) and that fluoxetine may increase hydroxybupropion and threohydrobupropion concentrations (15–18). Spontaneous postmarketing reports to the FDA are consistent with the possibility that fluoxetine inhibition of bupropion metabolism might yield seizures at lower bupropion dosages (19).

The absolute bioavailability of an oral dose in man has not been determined because an intravenous formulation for use in humans is not available. The absolute bioavailability of bupropion in animals is around 5% (20). Following oral administration of 200 mg of bupropion, 87% and 10% of the radioactive doses were excreted in the urine and feces, respectively, in man (21, 22). Plasma radioactivity concentration-time data obtained in the single-dose $^{14}$C metabolism study suggested that extensive presystemic elimination occurred in humans (21). Hence, the absolute bioavailability of an oral does of bupropion in man is expected to be low. Oral administration of bupropion is known to result in numerous dose-dependent adverse side effects, including seizure, headache/migraine, insomnia, dry mouth, dizziness, excessive sweating, anorexia, weight loss, constipation, sedation, tremor, and agitation (7). It is also reported that, due to its extensive first pass metabolism, high levels of bupropion metabolites may be associated with poor clinical outcome due to toxic effects involving dopaminergic systems (11).

Therefore, in view of the aforementioned deficiencies attendant with prior art methods of bupropion administration, it should be apparent that there still exists a need in the art for a safe and convenient method of administering bupropion to patients at safe and effective doses.

SUMMARY OF THE INVENTION

Accordingly, a major object of the present invention is to provide a method for safely and conveniently administering bupropion to a patient in need of such treatment, comprising intranasally administering an effective amount of bupropion to prevent or treat symptoms of withdrawal from nicotine and for the treatment of depression.

The objective of the present inventors is to improve bupropion bioavailability by administering bupropion via the nasal route in order to reduce the dose required for its beneficial effect. This will result in lower plasma concentrations of metabolites of bupropion, and therefore fewer side effects. Intranasal delivery will improve drug bioavailability by direct absorption into the circulation avoiding extensive hepatic first-pass metabolism which significantly lowers the plasma and brain concentrations of bupropion administered orally. Therefore, small doses of bupropion can be administered which will result in fewer side effects, and the drug will be more tolerable and more effective, both in treating patients suffering from depression, and in tobacco smokers engaged in treatment of their smoking addiction. Lipophilic drugs achieve higher brain levels after intranasal administration than after intravenous administration. The nasal route of administration of bupropion may help to enhance the effectiveness of bupropion in the brain (the site of action). Additionally, as bupropion is heavily metabolized by the liver, administration by the nasal route may help to reduce drug interactions with other drugs that are also extensively metabolized by the liver.

With the foregoing and other objects, advantages and features of the invention that will become hereinafter apparent, the nature of the invention is further explained in the following detailed description of the preferred embodiments of the invention and in the appended claims.

DETAILED DESCRIPTION OF THE PREFERRED EMBODIMENTS OF THE INVENTION

Thus, the present inventors have discovered a novel method for the delivery of bupropion to a patient in need of such treatment, comprising the intranasal administration of bupropion. This method offers significant clinical advantages over the prior art. More specifically, the inventors sought to provide a safe, effective and convenient treatment for administering bupropion to a patient in need of such treatment, which comprises the administration of bupropion intranasally, thus avoiding the side-effects associated with oral dosage forms. Specifically, smaller doses of bupropion can be administered through the nasal route, thus resulting in fewer side effects. By using the method of the present invention, the drug will become more tolerable and more effective, both in treating patients suffering from depression, and in tobacco smokers engaged in treatment of their smoking addiction.

The inventors have found that intranasal administration of bupropion effectively results in absorption of bupropion into plasma and directly into the central nervous system. Intranasal administration of bupropion is as effective as oral administration, but may be conveniently and painlessly self-administered by the patient, and at lower doses, thereby allowing a decreased incidence of side effects.

Figure 3:
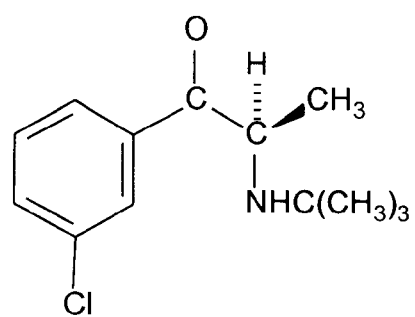
FIG. 3. Nonsuperimposable mirror images of Bupropion enantiomers.
Figure 3:
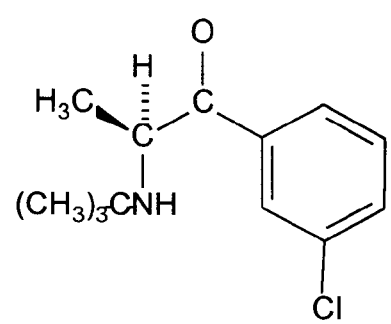

As used in the present invention, the term "bupropion" will be understood to refer to either (R)-bupropion, (S)-bupropion, or a racemic mixture of (R)- and (S)-bupropion (see FIG. 3).

According to the present invention, bupropion may be administered either as a free base, or in the form of a pharmaceutically acceptable salt thereof. Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-tolylsulfonic acids, and inorganic acids such as hydrochloric, sulfuric, phosphoric and sulfamic acids. In a particularly preferred embodiment, the pharmaceutically acceptable salt is bupropion HCl.

A still further aspect of this invention is a pharmaceutical composition of matter that comprises bupropion as described above, and/or pharmaceutically acceptable salts thereof, and pharmaceutically acceptable carriers therefor.

For therapeutic use in a smoking cessation program, bupropion, or its salt, can be conveniently administered in the form of a pharmaceutical composition containing bupropion, or its salt, and a pharmaceutically acceptable carrier therefor. Suitable carriers are well known to those skilled in the art and vary with the desired form and mode of administration of the pharmaceutical composition. Typically, the carrier may be a liquid, solution, suspension, gel, ointment, lotion, semi-solid, or vaporizable carrier, or combinations thereof. In a preferred embodiment, the carrier is a pharmaceutically acceptable aqueous carrier. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa., Eighteenth edition (1990), which is hereby incorporated by reference.

The compound of the invention or its salt may be formulated together with the carrier into any desired unit dosage form. Unit dosage forms such as solutions, suspensions, and water-miscible semisolids are particularly preferred.

Each carrier must be "acceptable" in the sense of being compatible with the other ingredients in the formulation and not injurious to the patient. The carrier must be biologically acceptable and inert. To prepare formulations suitable for intranasal administration, solutions and suspensions are sterilized and are preferably isotonic to blood.

The formulations may conveniently be presented in unit dosage form and may be prepared by any method known in the art. Such methods include the step of bringing the active ingredient into association with the carrier which itself may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art (see *Remington's Pharmaceutical Sciences*, seventeenth edition, ed. Alfonso R. Gennaro, Mack Publishing Company, Easton, Pa., Eighteenth edition (1990)).

In addition to the ingredients particularly mentioned above, the formulations of this invention may also include other agents conventional in the art for this type of pharmaceutical formulation.

The present invention is also directed to a method of treating depression, and to a method for preventing or treating the withdrawal symptoms associated with a program for treating those addicted to tobacco smoking, in a patient by treating that patient with an effective amount of bupropion intranasally. According to the present invention, the term "patient" will encompass any mammal requiring treatment with bupropion, particularly a human patient suffering from depression, or a human patient addicted to tobacco and engaged in a smoking cessation program.

The dosage of bupropion or pharmaceutically acceptable salts thereof in the compositions of the invention will vary depending on several factors, including, but not limited to, the age, weight, and species of the patient, the general health of the patient, the severity of the symptoms, whether the composition is being administered alone or in combination with other agents, the incidence of side effects and the like. The desired dose may be administered as 1 to 6 or more subdoses administered at appropriate intervals throughout the day. The compounds may be administered repeatedly over a period of months or years. Higher and lower doses may also be administered.

The daily dose may be adjusted taking into account, for example, the above-identified variety of parameters. Typically, racemic bupropion may be administered in an amount of up to about 400 mg/day. Preferably, the amount of racemic bupropion administered will not exceed 300 mg/day. However, other amounts may also be administered. Moreover, it may be possible to administer the individual enantiomers of bupropion at lower doses than the racemic mixture in order to achieve the same therapeutic effect.

To achieve good plasma concentrations, the bupropion may be administered, for instance, by intranasal administration of an approximate 0.1 to 1M solution of the active ingredient, optionally in saline.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents, e.g., other antidepressants, particularly tricyclic antidepressants. The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified.

EXAMPLE 1

In these experiments we will determine the bioavailability of bupropion after nasal administration and compare it to that after intravenous administration.

The nasal absorption of bupropion may be measured using an in vivo technique in rats. Rats are fasted overnight prior experimentation. Surgical procedures are performed under equithesin anesthesia (3 ml/kg, i.p.), an incision is made in the neck, and the trachea cannulated with polyethylene tubing (PF-260). A closed end tube is inserted through the esophagus to the posterior part of the nasal cavity to prevent drug from entering the esophagus. The nasopalatine passage is closed with an adhesive agent to prevent drainage of the drug from the nasal cavity to the mouth.

The jugular vein and femoral artery are cannulated with polyethylene tubing for intravenous drug administration and intra-arterial blood sampling.

Solutions of bupropion (2 mg free base bupropion/100 µl $H_2O$) are administered through the right nostril using a microsyringe. For intravenous administration, the same dose of the drug is injected into the jugular vein (1 ml/kg body weight). Blood samples after nasal or intravenous drug administration are collected before and at 2, 15, 30, 60 and 120 min after drug administration, centrifuged, and serum removed and stored (−80° C.) until analysis. Cerebrospinal fluid (CSF) is obtained as previously reported (32). Essentially, an incision is made in the skin over the occipital bone and the first layer of the muscle is cut. CSF is collected by cisternal puncture using a 25-gauge needle connected via PE-50 tubing. At specific time points 100 µl CSF is collected, frozen and stored (−80° C.) until analysis.

Bioavailability of nasally administered drug is calculated by comparing the plasma and CSF drug concentrations between nasal and intravenous delivery routes and expressed as a percentage of the intravenous bioavailability.

EXAMPLE 2: NASAL SPRAY SOLUTION

| | |
|---|---|
| Bupropion | 600 mg |
| Isotonic Saline | 30 ml |

The bupropion is dissolved in the sterile isotonic saline and the pH is adjusted to about 7.4. The solution is placed in a nasal administrator designed to deliver 0.1 ml of spray for each application. One spray in each nostril will deliver a total of 4 mg of bupropion

EXAMPLE 3: NASAL GEL (AQUEOUS)

| | |
|---|---|
| Bupropion | 100 mg |
| Methocel | 3 gm |
| Water | 100 gm |

Approximately 7 gm of water is heated to 80° C., and the methocel is dispersed in it with stirring. The bupropion is dissolved in 30 gm of water at 80° C., and the solution is mixed with the methocel dispersion. The resultant mixture is allowed to stand at room temperature for 3 hours. The gel is placed in an ointment tube equipped with a fine orifice and is applied in the nasal nares with a finger or cotton tipped applicator.

EXAMPLE 4

Since the rate and extent of drug absorption from the nasal cavity of the rat matches that of the human, we examined the disappearance (or absorption) of bupropion through the nasal cavity employing in vivo in situ technique described previously in rats. Briefly, male Sprague Dawley rats (275±25 g body weight) were anesthetized by intraperitoneal injection of equithesin. After incision was made in the neck, the trachea was cannulated with polyethylene tubing. A closed end tube was inserted through the esophagus to the posterior part of the nasal cavity to prevent drug from entering the esophagus. The nasopalatine passage is closed with an adhesive agent to prevent drainage of the drug from the nasal cavity to the mouth. A solution of bupropion (corresponding to 2 mg free base bupropion in 100 µl normal saline) was administered to the right nostril using a microsyringe with a 22 gauge needle attached to 3 mm of Silastic tubing. At appropriate time intervals, the nasal cavity was rinsed with 4 ml of water through the left nostril and collected from the right nostril. Water rinse was collected and stored at −70° C. until analysis.

Figure 1:
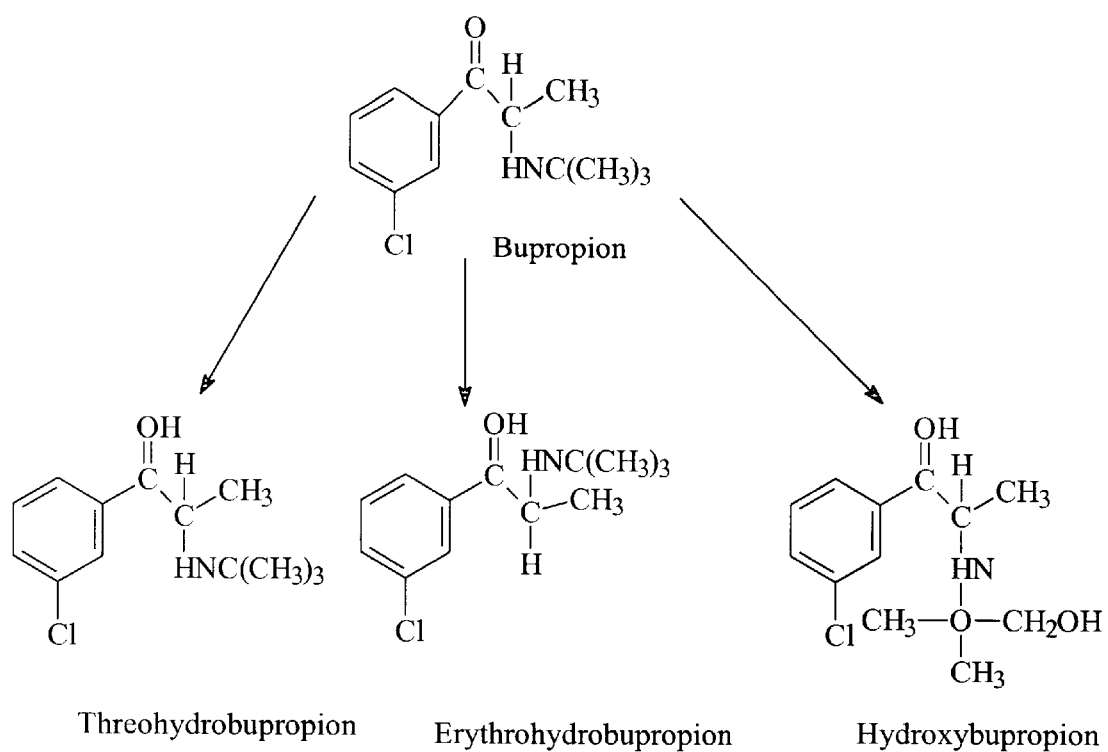
FIG. 1 depicts the structure of bupropion and its three major metabolites
Figure 2:
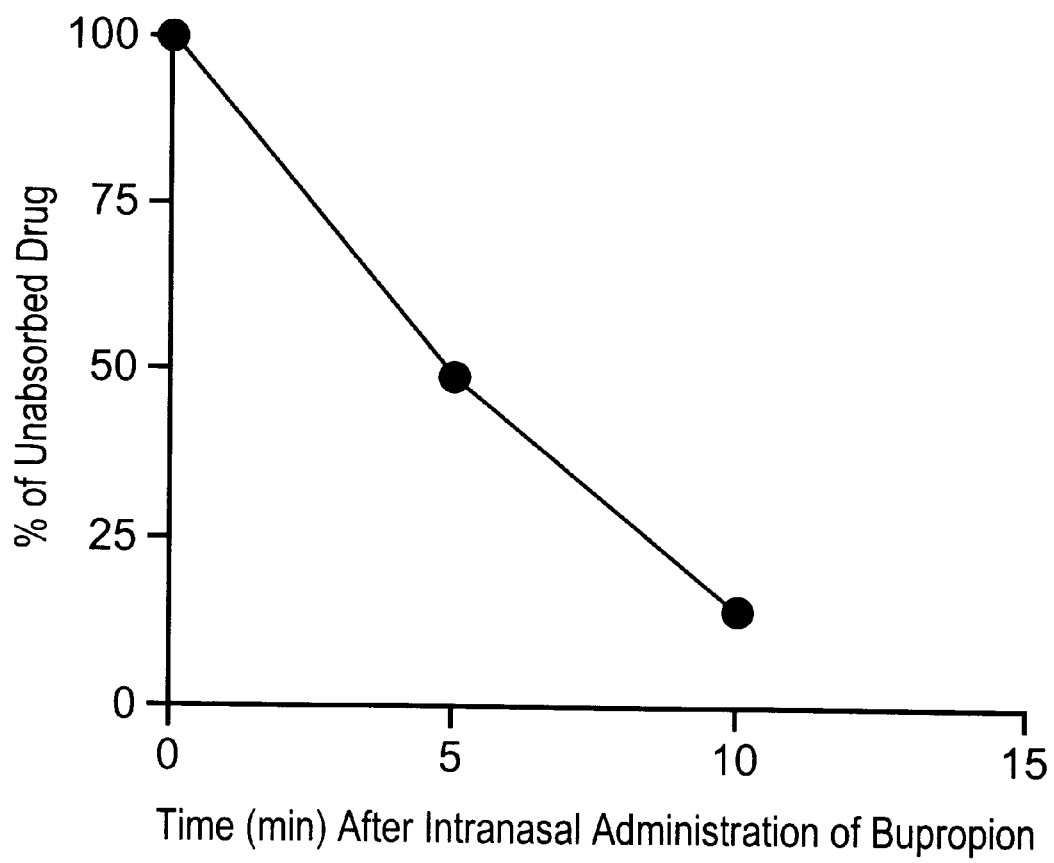
FIG. 2 illustrates bupropion disappearance (absorbance) following nasal application. Bupropion (2 mg free base/100 μl normal saline) was administered into the right nostril and at appropriate time intervals, the nasal cavity was rinsed with 4 ml of water applied through the left nostril and collected from the right nostril. Data are presented as the mean ±SEM (n=4 rats for each time point).

FIG. 2 shows the amount of bupropion remaining in the nasal cavity (unabsorbed) at different time intervals after bupropion administration. The results indicate that about 90% of administered bupropion disappeared (was absorbed) 10 minutes after nasal application.

These data indicate that bupropion is rapidly absorbed through the nasal passage, and would be expected to increase its brain bioavailability (site of action) at least 15–20 fold compared to that after oral administration.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method for delivering bupropion to a patient comprising intranasally administering an effective amount of a pharmaceutical composition comprising bupropion, or a pharmaceutically acceptable salt thereof, and a pharmaceutically acceptable carrier therefor.

2. A method according to claim 1, wherein the pharmaceutically acceptable salt of bupropion is bupropion HCl.

3. A method according to claim 1, wherein the bupropion is (R)-bupropion.

4. A method according to claim 1, wherein the bupropion is (S)-bupropion.

5. A method according to claim 1, wherein the bupropion is a racemic mixture of (R)-bupropion and (S)-bupropion.

6. A method according to claim 1, wherein the carrier is aqueous.

7. A method for treating addiction to tobacco comprising intranasally administering to a patient in need of said treatment an effective amount of bupropion, or a pharmaceutically acceptable salt thereof.

8. A method according to claim 7, wherein the wherein the pharmaceutically acceptable salt of bupropion is bupropion HCl.

9. A method according to claim 7, wherein the bupropion is (R)-bupropion.

10. A method according to claim 7, wherein the bupropion is (S)-bupropion.

11. A method according to claim 7, wherein the bupropion is a racemic mixture of (R)-bupropion and (S)-bupropion.

12. A method according to claim 7, wherein the carrier is aqueous.

13. A method for treating depression comprising intranasally administering to a patient in need of said treatment an effective amount of bupropion, or a pharmaceutically acceptable salt thereof.

14. A method according to claim 13, wherein the pharmaceutically acceptable salt of bupropion is bupropion HCl.

15. A method according to claim 13, wherein the bupropion is (R)-bupropion.

16. A method according to claim 13, wherein the bupropion is (S)-bupropion.

17. A method according to claim 13, wherein the bupropion is a racemic mixture of (R)-bupropion and (S)-bupropion.

18. A method according to claim 13, wherein the carrier is aqueous.

19. A pharmaceutical composition suitable for intranasal administration comprising bupropion, or a pharmaceutically acceptable salt thereof, and a pharmaceutically and intranasally acceptable carrier therefor.

20. A composition according to claim 19, wherein the pharmaceutically acceptable salt of bupropion is bupropion HCl.

21. A composition according to claim 19, wherein the bupropion is (R)-bupropion.

22. A method according to claim 19, wherein the bupropion is (S)-bupropion.

23. A method according to claim 19, wherein the bupropion is a racemic mixture of (R)-bupropion and (S)-bupropion.

* * * * *